(12) United States Patent
Casteleyn et al.

(10) Patent No.: US 11,305,071 B2
(45) Date of Patent: Apr. 19, 2022

(54) MULTIPLE INJECTION NEEDLE ASSEMBLY

(71) Applicant: Terumo Europe N.V., Leuven (BE)

(72) Inventors: Pieter Casteleyn, Herent (BE); Ludo Daniels, Tongeren (BE); Veerle Royen, Tongeren (BE); Christian Fripon, Haasrode (BE)

(73) Assignee: TERUMO EUROPE N.V., Leuven (BE)

( * ) Notice: Subject to any disclaimer, the term of this patent is extended or adjusted under 35 U.S.C. 154(b) by 199 days.

(21) Appl. No.: 16/480,502

(22) PCT Filed: Jan. 24, 2018

(86) PCT No.: PCT/EP2018/051750
§ 371 (c)(1),
(2) Date: Jul. 24, 2019

(87) PCT Pub. No.: WO2018/138164
PCT Pub. Date: Aug. 2, 2018

(65) Prior Publication Data
US 2019/0381257 A1 Dec. 19, 2019

(30) Foreign Application Priority Data
Jan. 24, 2017 (EP) .................................... 17152798

(51) Int. Cl.
*A61M 5/32* (2006.01)
(52) U.S. Cl.
CPC ................................ *A61M 5/3298* (2013.01)
(58) Field of Classification Search
CPC ...... A61M 5/32; A61M 5/329; A61M 5/3291; A61M 5/3295; A61M 5/3298; A61M 5/3293
See application file for complete search history.

(56) References Cited

U.S. PATENT DOCUMENTS

| 2003/0050602 A1 | 3/2003 | Pettis et al. |
| 2013/0102954 A1* | 4/2013 | Choi ..................... A61H 39/08 604/21 |
| 2014/0128810 A1 | 5/2014 | Ozawa et al. |

FOREIGN PATENT DOCUMENTS

| KR | 10-2014-0012140 A | 1/2014 |
| WO | WO2006/118804 A1 | 11/2006 |
| WO | WO2009/035680 A1 | 3/2009 |

OTHER PUBLICATIONS

International Search Report for PCT Patent App. No. PCT/EP2018/051750 (dated Jun. 28, 2018).

* cited by examiner

*Primary Examiner* — Jason E Flick
(74) *Attorney, Agent, or Firm* — Kenealy Vaidya LLP

(57) ABSTRACT

Some embodiments are directed to a needle assembly including at least N injection needles where N is at least four and a multiple of two. The needle assembly also includes a first liquid port adapted to be connected to an injection device, and N second liquid ports connected to one of the N injection needles. N/2 main liquid pathways each have an entrance connected to the first liquid port and an exit, further including N/2 secondary liquid pathways that have two extremities each opening on one of the N second liquid ports, and a mid portion connected to the exit of one of the main liquid pathways. The main liquid pathways and the secondary liquid pathways define N liquid flow paths between the first liquid port and the N second liquid ports dimensioned so a pressure drop between them is similar.

21 Claims, 2 Drawing Sheets

MULTIPLE INJECTION NEEDLE ASSEMBLY

CROSS REFERENCE TO RELATED PARAGRAPHS

This application is a national phase filing under 35 C.F.R. § 371 of and claims priority to PCT Patent Application No. PCT/EP2018/051750, filed on Jan. 24, 2018, which claims the priority benefit under 35 U.S.C. § 119 of European Patent Application No. 17152798.9, filed on Jan. 24, 2017, the contents of each of which are hereby incorporated in their entireties by reference.

BACKGROUND

The presently disclosed subject matter relates to an injection needle assembly including at least N-number of injection needles where N is a multiple of two. This injection needle assembly is intended for use with a medical injection device such as a syringe.

Injection needle assemblies including more than one injection needle are useful to treat large areas of a body, for example skin or a muscle. Some examples of multiple injection needle assemblies are known from the related art. For example, document US 2013-102954 discloses injection needle assemblies including four or sixteen injection needles to perform meso therapy.

However, these related art multiple injection needle assemblies include injection needles arranged at the corner of a square, which does not allow to inject an injection product in a non-square portion of a body, such as a narrow muscle, a portion of a face or a wrinkle. As a result, it is desired to treat such non-squared portions of a body using several injection needles and several injection devices, which is a waste of time and money.

There is thus a need for an injection needle assembly overcoming these drawbacks. In other words, there is a need for an injection needle assembly including more than one needle where the needles can adopt any arrangement and where all or most of the injection needles inject a similar quantity of an injection product.

SUMMARY

Some embodiments are therefore directed to an injection needle assembly including:
- at least N injection needles where N is at least four and a multiple of two,
- a first liquid port adapted to be connected to an injection device,
- N second liquid ports, each connected to one of the N injection needles, $$\frac{N}{2}$$

main liquid pathways each having an entrance connected to the first liquid port and having an exit, characterized in that it further includes $$\frac{N}{2}$$

secondary liquid pathways including:
- two extremities each opening on one of the N second liquid ports, and
- a mid portion connected to the exit of one of the main liquid pathways;

and in that the main liquid pathways and the secondary liquid pathways define N liquid flow paths between the first liquid port and the N second liquid ports and are dimensioned so that a pressure drop between the first liquid port and each of the N second liquid ports is similar.

Thanks to the specific architecture of the main and secondary liquid pathways and thanks to the similar pressure drop between the N liquid flow paths, a similar flow rate is achieved at all or most of the second liquid ports during injection, and thus at all or most of the injection needles. Due to that, a homogeneous injection may be performed with at least four injection needles at the same time, which optimizes the diagnostic, cosmetic, therapeutic or prophylactic effect of the injection product. In addition, the dead volume, i.e. the amount of injection product remaining in the injection needle assembly after the end of injection remains limited even when N becomes larger than four. Finally, the injection needle assembly according to the presently disclosed subject matter is not limited a square-like arrangement and allows to design a wide range of injection needles arrangements, such as circular, linear or others, while preserving a similar injection flow rate. This wide range of injection needle arrangements is valuable to design injection needle assemblies adapted to specific areas of a body.

In the sense of the presently disclosed subject matter, the word "similar" may be the same within ±10%, in some embodiments ±5%, and in some embodiments ±2%, which contributes to ensure an homogeneous injection to the injection area. In addition, the injection needle assembly according to the presently disclosed subject matter may include additional injection needles, beyond the N injection needles, as detailed below.

Advantageously, the majority of the N injection needles are aligned in a straight line and in some embodiments, all or most of the injection needles are aligned in a straight line. Such an alignment is valuable to treat linear portion of a body, such as narrow muscles or wrinkles.

In some embodiments, the main liquid pathways have a similar cross-section surface between each other, and the secondary liquid pathways have a similar cross-section surface between each other. In some embodiments, the cross section surface of the main liquid pathways and the secondary liquid pathways are constant over their length, respectively. In some embodiments, the main liquid pathways and the secondary liquid pathways have the same constant cross section surface. Alternatively, the cross section surface of a main liquid pathway may be twice as large as the cross section surface of a secondary liquid pathway.

Advantageously, the injection needle assembly according to the present embodiment includes an additional needle, an additional second liquid port connected to the additional needle, and an additional liquid flow path between the first liquid port and the additional second liquid port, wherein the additional liquid flow path is dimensioned so that a pressure drop between the first liquid port and the additional second liquid port is similar to the pressure drop between the first liquid port and each of the N second liquid ports.

This allows to design injection needle assemblies with a wide range of injection needles arrangements including an uneven number of injection needles, such as five, seven or more, while preserving a similar injection flow rate between all or most of the injection needles.

Advantageously, the main liquid pathways and the secondary liquid pathways are formed in the same piece of material, and/or include the same surface condition. Such a material may be PMMA or PC.

Another aspect of the presently disclosed subject matter is an injection needle assembly including:
- at least N injection needles where N is at least two and a multiple of two,
- a first liquid port adapted to be connected to an injection device,
- N second liquid ports, each connected to one of the N injection needles, $$\frac{N}{2}$$

main liquid pathways each having an entrance connected to the first liquid port and having an exit,
characterized in that it further includes $$\frac{N}{2}$$

secondary liquid pathways including:
- two extremities each opening on one of the N second liquid ports, and
- a mid portion connected to the exit of one of the main liquid pathways;

and in that the main liquid pathways and the secondary liquid pathways define N liquid flow paths between the first liquid port and the N second liquid ports and are dimensioned so that a pressure drop between the first liquid port and each of the N second liquid ports is similar.

Another aspect of the presently disclosed subject matter is an injection needle assembly including:
- at least N injection needles where N is at least two and a multiple of two,
- a first liquid port adapted to be connected to an injection device,
- N second liquid ports, each connected to one of the N injection needles, $$\frac{N}{2}$$

main liquid pathways each having an entrance connected to the first liquid port and having an exit,
characterized in that it further includes $$\frac{N}{2}$$

secondary liquid pathways including:
- two extremities each opening on one of the N second liquid ports, and
- a mid portion connected to the exit of one of the main liquid pathways; and in that the main liquid pathways and the secondary liquid pathways define N liquid flow paths between the first liquid port and the N second liquid ports and are dimensioned so that a flow rate at each of the N second liquid ports is similar.

In other words, some embodiments are related to an injection needle assembly including:
- at least N injection needles where N is at least two, and in some embodiments at least four, and a multiple of two,
- a first liquid port adapted to be connected to an injection device,
- N second liquid ports, each connected to one of the N injection needles, $$\frac{N}{2}$$

main liquid pathways each having an entrance connected to the first liquid port and having an exit,
characterized
in that it further includes $$\frac{N}{2}$$

secondary liquid pathways including:
- two extremities each opening on one of the N second liquid ports, and
- a mid portion connected to the exit of one of the main liquid pathways;

and in that the main liquid pathways and the secondary liquid pathways define N liquid flow paths between the first liquid port and the N second liquid ports, which present a similar length and/or similar cross section surface and/or similar wall surface condition (including roughness), and/or similar trajectory profile, and/or similar junction shape between the main liquid pathways and the secondary liquid pathway. Some embodiments provide an injection needle assembly with all or most of the N liquid flow paths having the same or almost the same upstream channel in shape and length and cross section (similar main liquid pathways), and/or the same or almost the same downstream channel in profile and/or length and/or cross section (similar secondary liquid pathways), and/or same channel wall characteristics (roughness, material), and/or same connection shape between main and secondary liquid pathways (in angle, cross section . . . ). Therefore, the injection needle assembly provides during injection the same flow rate between all or most of the N needles.

A last aspect of the presently disclosed subject matter is an injection device including an injection needle assembly according to the first aspect or the other aspects of the presently disclosed subject matter.

BRIEF DESCRIPTION OF THE DRAWINGS

Further advantages of some embodiments of the presently disclosed subject matter will become apparent from the following detailed description and drawings, in which.

DETAILED DESCRIPTION

The present injection needle assembly is intended to be used for the injection of an injection product in a patient or an animal by multiple injection point. The injection product may be a liquid or a gel and may include any therapeutic, diagnostic, cosmetic or prophylactic product, but is in some embodiments a cosmetic product such as hyaluronic acid. In addition, the injection could be intradermal, subcutaneous or intramuscular but is in some embodiments subcutaneous or intradermal.

The injection needle assembly is intended to be used with an injection device, such as a syringe, an auto-injector or a reusable injector.

Figure 1:
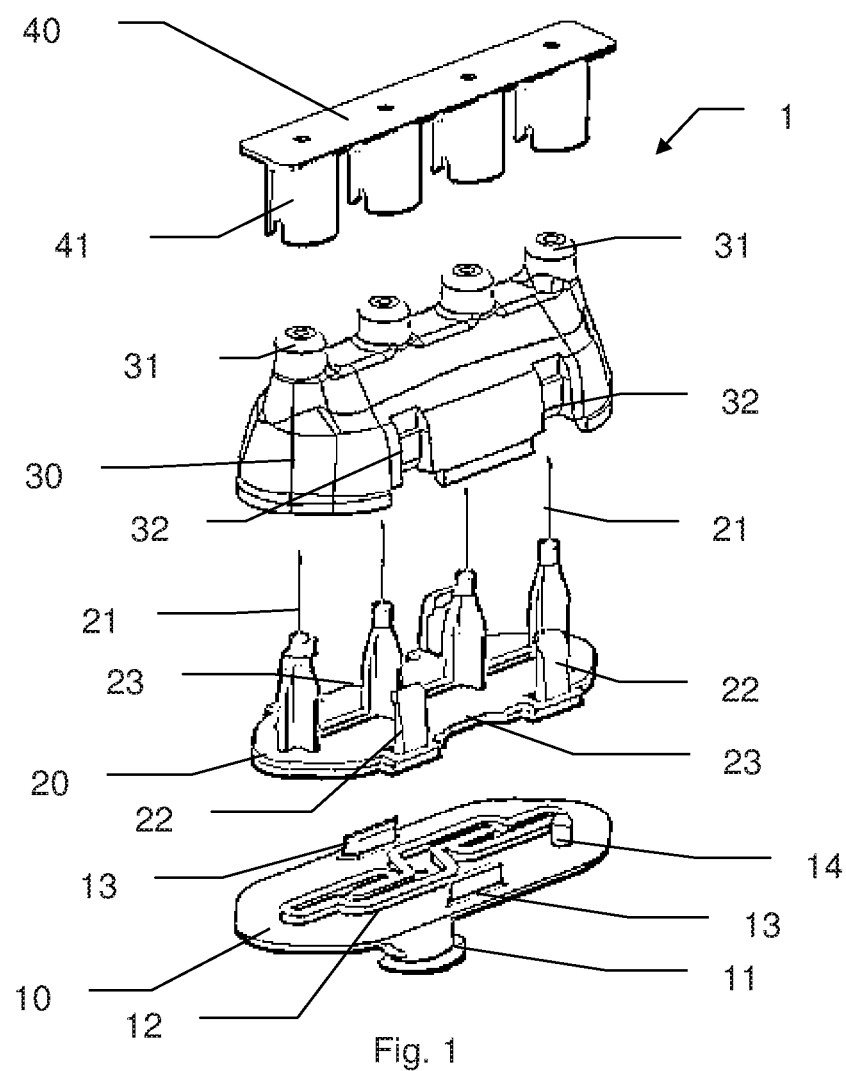
FIG. 1 is an exploded view of an injection needle assembly according to an embodiment of the presently disclosed subject matter including four injection needles.

Now referring to FIG. 1, and from proximal to distal or from bottom to top in the view of FIG. 1, an embodiment of an injection needle assembly 1 includes a base plate 10, a needles plate 20, a cover 30 and a needles shield 40.

The base plate 10 includes on its proximal face an adaptor 11 in the form of a female luer lock adaptor intended to be connected to a male luer lock adaptor of a prefilled syringe (not shown). However, any other adaptor can be used in order to secure the injection needle assembly 1 to the injection device. For example, it can be fixed to the tip of a syringe by a luer slip connection and or be glued, clipped or welded. It can also be screwed in an adapted receiving part of an injector. The adaptor 11 can be hollow so as to allow a fluid communication between the injection device and the base plate 10.

The base plate 10 is further provided on its distal face with an embossed design 12 defining a liquid circulation area as explained later, two protruding tabs 13 and a centring stud 14.

The needles plate 20 includes on its distal face four aligned injection needles 21 which are glued to the needles plate 20. The needles plate 20 further includes four protruding tabs 22 (three are visible in FIG. 1), two circumferential recesses 23 and an axial hole (not visible). The circumferential recesses 23 are intended to accommodate the protruding tabs 13 of the base plate 10 and the axial hole is intended to accommodate the centring stud 14 of the base plate 10, when the needles plate 20 is assembled to the base plate 10, as detailed below.

On its proximal face, the needles plate 20 can have an embossed design (not visible) corresponding or complementary to the embossed design 12 of the base plate 10. The needles 21 can be open on the proximal face of the needles plate 20 so as to allow a fluid communication with the base plate 10 when the injection needle assembly 1 is assembled.

The cover 30 includes a hollow body in the form of a crest, four distal openings 31 with a cylindrical shape, aligned with the injection needles 21 and four circumferential recesses 32 aligned with the protruding tabs 22 of the needles plate 20 and having a geometry complementary to the geometry of the protruding tabs 22.

The needles shield 40 includes four sheaths 41 on its proximal surface, the four sheaths 41 being aligned with the four distal openings 31 of the cover 30 and having similar dimensions.

The base plate 10, the needles plate 20 and the cover 30 are in some embodiments made of a rigid plastic material of medical grade such as Poly(methyl methacrylate) (PMMA) or alternatively Polycarbonate (PC). They are produced by injection moulding and the injection needles 21 are glued to the needles plate 30. Alternatively, the needles 21 may be overmoulded, staked or screwed to the needles plate 20. The needle shield 40 is made of a plastic material as mentioned above or an elastomer such as natural rubber, butyl rubber, halo butyl rubber or silicon rubber.

The injection needle assembly 1 according to some embodiments embodiments is assembled as follows: the needles plate 20 is fitted on the base plate 10 such that the protruding tabs 13 of the base plate 10 are accommodated in the circumferential recesses 23 of the needles plate 20 and the centring stud 14 is accommodated in the axial hole of the needles plate 20. The needles plate 20 and the base plate 10 now fitted together can then be welded by ultrasonic welding, in order to close and seal the liquid circulation area defined at least by the embossed design 12 of the base plate 10.

The cover 30 is then fitted onto the needles plate 20 and the protruding tabs 22 of the needles plate 20 interlock the circumferential recesses 32 of the cover 30 such as to secure the cover 30 to the needles plate 20. In addition, the injection needles 21 of the needles plate 20 are accommodated through the distal opening 31 in order to protrude in the distal direction beyond the cover 30.

The needle shield 40 is finally placed onto the cover 30: the sheaths 41 are force-fitted onto the distal openings 31 of the cover 30 and at least the tips of the injection needles 21 are accommodated and protected inside the sheaths 41.

The injection needle assembly 1 is then ready for the next applicable phases, such as sterilization, packaging, shipping, storage and use.

Figure 2:
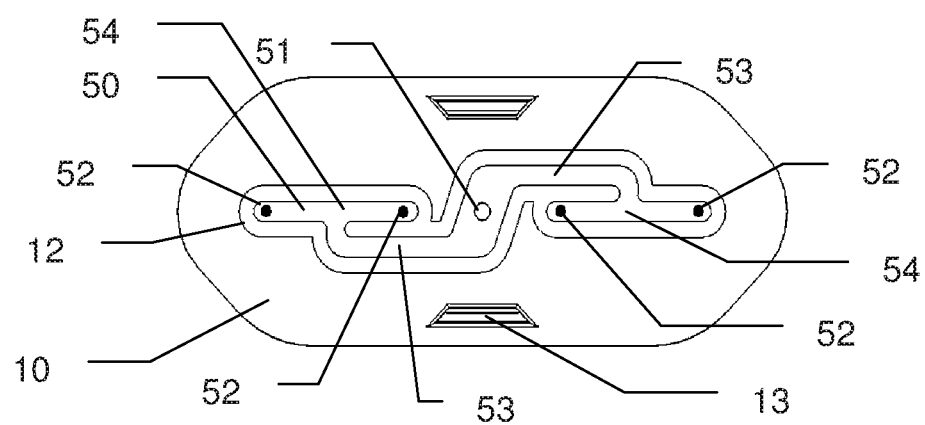
FIG. 2 is a detailed view of a liquid circulation area of an injection needle assembly according to FIG. 1.

Now referring to FIG. 2, the embossed design 12 defines a liquid circulation area 50 including a first liquid port 51 connected to the adaptor 11, four second liquid ports 52 connected or opening to the needles 21 when the injection needle assembly 1 is assembled, two main liquid pathways 53 extending from the first liquid port 51 in opposite radial directions and two secondary liquid pathways 54. The second liquid ports 52 are aligned and may represent the location of the injection needle opening on the proximal face of the needles plate 21.

The main liquid pathways 53 include a first extremity or entrance connected to the first liquid port 51 and a second extremity or exit connected to a 20 mid-portion of a secondary liquid pathway 54. Each secondary liquid pathway 54 has two extremities, each of them accommodating or opening on a second liquid port 52. In the liquid circulation area 50 according to some embodiments, the main liquid pathways 53 and the second liquid pathways 54 are symmetric around an axis formed by the first liquid port 51.

Both couples of a main liquid pathway 53 and a secondary liquid pathway 54 of the injection needle assembly 1 define a liquid flow path allowing an injection product to flow from an injection device to an injection needle. Each liquid flow path has a similar profile and a similar length, and thus shows a similar pressure loss when an injection product circulates through it.

The use of an injection needle assembly 1 according some embodiments is now explained with reference to FIGS. 1 & 2. The injection needle assembly 1 is first extracted from its packaging for example by a medical staff member and is fixed or screwed by the adaptor 11 to the luer lock connector of a syringe filled or prefilled with an injection product. The needle shield 40 is then removed to reveal at least the tip of the injection needles 21. The injection needle assembly is then primed by the medical staff member: the plunger rod of the syringe is moved distally in order to fill-up the liquid circulation area 50 with the injection product, thus removing air from the liquid circulation area 50.

The skin of the patient is then punctured by the injection needles 21 which penetrate in or under the skin to an injection area. The plunger rod is distally moved again, and the injection product flows equally, from the first liquid port 51 toward the main liquid pathways 53 and reaches the secondary liquid pathways 54 by their mid-portion. The injection fluid is then distributed equally, i.e. with a similar flow rate and in similar quantities between the two second liquid ports 52 through each secondary liquid pathway 54, thanks to the two similar flow paths with similar pressure loss. As a result, a similar flow rate of the injection product is achieved in each needle 21 and a homogeneous quantity of injection fluid is injected in the injection area of a patient. As a result, the cosmetic, therapeutic, diagnostic or prophylactic effect of the injection fluid is maximized and a specific injection area of a patient can be treated in a single injection, which saves time and injection material.

Figure 3:
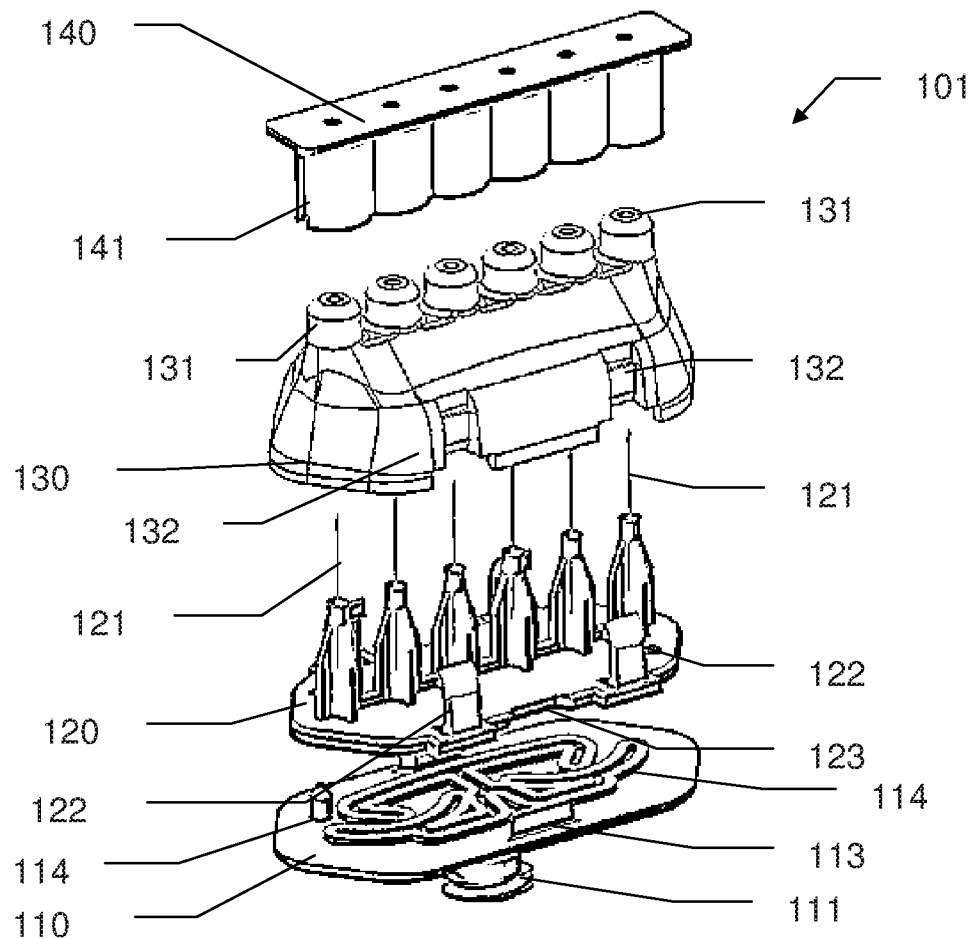
FIG. 3 is an exploded view of an injection needle assembly according to another embodiment of the presently disclosed subject matter including six injection needles.
Figure 4:
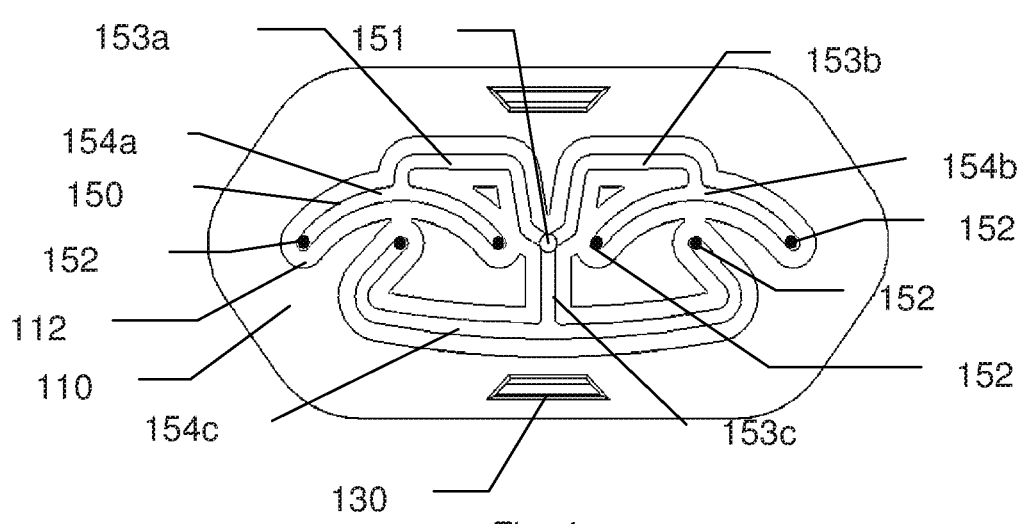
FIG. 4 is a detailed view of a liquid circulation area of an injection needle assembly according to FIG. 3.

The injection needle assembly 101 according to another embodiment is similar to the injection needle assembly 1 according to the previously described embodiment with the differences that it includes six needles instead of four and that the embossed design of the base plate defines a different and more complex liquid circulation area. With reference to FIGS. 3 and 4, similar parts of the injection needle assembly 2 are numbered with the same reference numbers plus 100. For example, the base plate according to this embodiment is 110.

Now regarding FIG. 4, the embossed design 112 defines a liquid circulation area 150 including a first liquid port 151 connected to the adaptor 111, six second liquid ports 152 connected to the needles 121 when the injection needle assembly 101 is assembled.

On a top portion, as viewed in FIG. 4, it further includes two main liquid pathways 153a and 153b with a stepped profile which is symmetric according to a planar symmetry and connected by an extremity or entrance to the first liquid port 151. These main liquid pathways 153a-153b are each connected by another extremity or exit to one of the two similar secondary liquid pathways 154a-154b. These secondary liquid pathways have an identical profile in the form of an arc of a circle, with a second injection port 152 located or accessible at each extremity of the arc of a circle. The secondary liquid pathways 154a-154b are connected to the main liquid paths 153a-153b by a mid-portion or a tangent point on the most upper portion of the arc of a circle as viewed in FIG. 4. Consequently, each couple of a main liquid pathway 153a-153b and a secondary liquid pathway 154a-154b defines a symmetric and similar liquid flow path, with a similar profile, a similar length, a similar cross-section and a similar pressure loss.

On a bottom portion, as viewed in FIG. 4, the liquid circulation area 150 defines a third main liquid pathway 153c showing a different, linear profile. It extends from the first injection port by one extremity or entrance and is connected by another extremity or exit to a third secondary liquid pathway 153c having the profile of a fork, namely with two extremities pointing toward the top portion of the base plate 110 and in particular toward the arcs of a circle of the first two secondary liquid pathways 154a-154b. Each extremity is provided with or opens to a second injection port 152. The third main liquid pathway 153c is on a plane crossing the base plate 110 in the middle and the third secondary liquid pathway is symmetric in view of this plane.

As a result of the specific profile of the third main liquid pathway 153c and the third secondary liquid pathway 154c, all or most of the second injection points 152 are aligned. In addition, the couple of the third main liquid pathway 153c and the third secondary liquid pathway 154c defines a third liquid flow path with a different profile than the first two liquid flow paths of the top portion of the base plate 110. However, the length, the cross-section and the pressure loss of this third liquid flow path are similar to the two other liquid flow paths of the top portion of the liquid circulation area 150. This ensures a similar injection flow rate for all or most of the aligned injection needles 121 when the injection needle assembly 101 is used to inject an injection product to a patient or an animal.

Computer Simulation

In order to demonstrate that the presently disclosed subject matter allows a similar injection flow rate for all or most of the injection needles, a computerized mock-up of the injection needle assembly according to the some embodiments of the presently disclosed subject matter and FIGS. 3 and 4 has been performed. The different pathways of the liquid circulation area 150 have a rectangular section and a total length of 21.061 mm and a total volume of 17.45 mm$^3$.

A fluid simulating an injection product such as a non Newtonian fluid with a consistency index smaller than 1 was used.

The liquid circulation area is initially filled with air. The above detailed fluid is inserted in a syringe as an injection device. When the injection is simulated or performed, some time is desired before the fluid reaches the different second liquid ports. These time periods between the start of the injection (the distal movement of a plunger rod) and the entrance of the fluid into an injection needle are summarized in table 1 below.

| Outlet no | Time [s] | Time difference w.r.t. largest time [s] | Corresponding volume [×10$^{-3}$ ml] |
|---|---|---|---|
| 1 | 2.171 | 0.117 | 0.972 |
| 2 | 2.288 | 0.000 | 0.000 |
| 3 | 2.137 | 0.151 | 1.256 |
| 4 | 2.128 | 0.160 | 1.329 |
| 5 | 2.280 | 0.008 | 0.067 |
| 6 | 2.168 | 0.120 | 0.996 |

These results demonstrate a very limited time shift between each second liquid port and thus between each injection needle. Consequently, it can be deduced that the flow rate between each injection needle is similar or almost identical.

Although the presently disclosed subject matter has been described and illustrated in detail, it is clearly understood that the same is by way of illustration and example and is not to be taken by way of limitations, the scope of the presently disclosed subject matter being limited only by the terms of the appended claims.

The invention claimed is:

1. An injection needle assembly, comprising:
   at least N injection needles where N is at least four and a multiple of two,
   a first liquid port adapted to be connected to an injection device,
   N second liquid ports, each connected to only one of the N injection needles, $$\frac{N}{2}$$

main liquid pathways each having an entrance connected to the first liquid port and having an exit,
   wherein the injection needle assembly further comprises $$\frac{N}{2}$$

secondary liquid pathways, further including:
two extremities each opening on one of the N second liquid ports, and
a mid portion connected to the exit of one of the main liquid pathways;
and wherein the main liquid pathways and the secondary liquid pathways define N liquid flow paths between the first liquid port and the N second liquid ports and are dimensioned so that a pressure drop between the first liquid port and each of the N second liquid ports is between ±10%.

2. The injection needle assembly according to claim 1, wherein the pressure drop between the first liquid port and each of the second liquid ports is within 5%.

3. The injection needle assembly according to claim 1, wherein a length of any of the N liquid flow paths is between ±10%.

4. The injection needle assembly according to claim 1, wherein a length of any of the N liquid flow paths is within ±10% of each other.

5. The injection needle assembly according to claim 1, wherein a majority of the N injection needles are aligned in a straight line.

6. The injection needle assembly according to claim 5, wherein all the injection needles are aligned in a straight line.

7. The injection needle assembly according to claim 1, wherein:
the main liquid pathways have a substantially constant cross-section surface between each others, and
the secondary liquid pathways have a substantially constant cross-section surface between each others.

8. The injection needle assembly according to claim 7, wherein:
the main liquid pathways have a cross section surface within ±10% between each others, and
the secondary liquid pathways have a cross section surface within ±10% between each others.

9. The injection needle assembly according to claim 1, further comprising an additional second needle, an additional second liquid port connected to the additional second needle, and an additional second liquid flow path between the first liquid port and the additional second liquid port,
wherein the additional liquid flow path is dimensioned so that a pressure drop between the first liquid port and the additional second liquid port is between ±10% to the pressure drop between the first liquid port and each of the N second liquid ports.

10. The injection needle assembly according to claim 1, wherein the main liquid pathways and the secondary liquid pathways are formed in a same piece of material.

11. The injection needle assembly according to claim 1, wherein the main liquid pathways and the secondary liquid pathways are arranged in a plane perpendicular to an injection axis.

12. An injection needle assembly, comprising:
at least N injection needles where N is at least two and a multiple of two,
a first liquid port adapted to be connected to an injection device,
N second liquid ports, each connected to only one of the N injection needles, $$\frac{N}{2}$$

main liquid pathways each having an entrance connected to the first liquid port and having an exit,
wherein the injection needle further comprises $$\frac{N}{2}$$

secondary liquid pathways, further including:
two extremities each opening on one of the N second liquid ports, and
a mid portion connected to the exit of one of the main liquid pathways;
and wherein the main liquid pathways and the secondary liquid pathways define N liquid flow paths between the first liquid port and the N second liquid ports and are dimensioned so that a pressure drop between the first liquid port and each of the N second liquid ports is between ±10%.

13. An injection device comprising an injection needle assembly according to claim 1.

14. An injection device comprising an injection needle assembly according to claim 12.

15. The injection needle assembly according to claim 5, wherein:
the main liquid pathways have a substantially constant cross-section surface between each others, and
the secondary liquid pathways have a substantially constant cross-section surface between each others.

16. The injection needle assembly according to claim 5, further comprising an additional second needle, an additional second liquid port connected to the additional second needle, and an additional second liquid flow path between the first liquid port and the additional second liquid port,
wherein the additional liquid flow path is dimensioned so that a pressure drop between the first liquid port and the additional second liquid port is between ±10% to the pressure drop between the first liquid port and each of the N second liquid ports.

17. The injection needle assembly according to claim 7, further comprising an additional second needle, an additional second liquid port connected to the additional second needle, and an additional second liquid flow path between the first liquid port and the additional second liquid port,
wherein the additional liquid flow path is dimensioned so that a pressure drop between the first liquid port and the additional second liquid port is between ±10% to the pressure drop between the first liquid port and each of the N second liquid ports.

18. The injection needle assembly according to claim 5, wherein the main liquid pathways and the secondary liquid pathways are formed in a same piece of material.

19. The injection needle assembly according to claim 7, wherein the main liquid pathways and the secondary liquid pathways are formed in a same piece of material.

20. The injection needle assembly according to claim 9, wherein the main liquid pathways and the secondary liquid pathways are formed in a same piece of material.

21. An injection needle assembly, comprising:
at least N injection needles where N is at least four and a multiple of two,
a first liquid port adapted to be connected to an injection device,
N second liquid ports, each connected to one of the N injection needles, $$\frac{N}{2}$$

main liquid pathways each having an entrance connected to the first liquid port and having an exit, wherein the injection needle assembly further comprises $\frac{N}{2}$ secondary liquid pathways, further including:
- two extremities each opening on one of the N second liquid ports, and
- a mid portion connected to the exit of one of the main liquid pathways;
- wherein the main liquid pathways and the secondary liquid pathways define N liquid flow paths between the first liquid port and the N second liquid ports and are dimensioned so that a pressure drop between the first liquid port and each of the N second liquid ports is between ±10%, and
- wherein each of the N liquid flow paths are dimensioned at an angle with respect to an adjacent one of the N liquid flow paths.

* * * * *